(12) United States Patent
Tse (10) Patent No.: US 11,179,233 B2
(45) Date of Patent: Nov. 23, 2021

(54) STAGING ASSEMBLY FOR SPECIMEN IMAGING SYSTEM (71) Applicant: PerkinElmer Health Sciences, Inc., Waltham, MA (US)

(72) Inventor: Shing Chi Ricky Tse, Providence, RI (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 450 days.

(21) Appl. No.: 16/053,134

(22) Filed: Aug. 2, 2018

(65) Prior Publication Data
US 2020/0038163 A1   Feb. 6, 2020

(51) Int. Cl.
*A61D 7/04* (2006.01)
*A61D 3/00* (2006.01)
*A61M 16/01* (2006.01)
*A61M 16/00* (2006.01)

(52) U.S. Cl.
CPC ............... *A61D 7/04* (2013.01); *A61D 3/00* (2013.01); *A61M 16/009* (2013.01); *A61M 16/01* (2013.01)

(58) Field of Classification Search
CPC .... A61M 16/009; A61M 16/01; A61M 16/06; A61M 2250/00; A61D 3/00; A61D 7/04; A01K 1/03; A01K 1/031; A61B 6/508; A61B 5/055; A61B 6/032; A61B 6/037; A61B 2503/40; F17D 1/00; F17D 1/02; F17D 1/04; Y10T 137/8593; Y10T 137/85938

USPC ....................... 128/200.24, 203.12
See application file for complete search history.

(56) References Cited

U.S. PATENT DOCUMENTS

| 10,632,271 B1* | 4/2020 | Leevy | ............... A61D 7/04 |
| 2015/0047724 A1* | 2/2015 | Leevy | ............... A61D 7/04 137/561 A |

FOREIGN PATENT DOCUMENTS

EP    1478423 A1   11/2004

OTHER PUBLICATIONS

Oct. 28, 2019 (WO) ISR & WO PCT Application No. PCT/US2019/043215.

* cited by examiner

Primary Examiner — Elliot S Ruddie
(74) Attorney, Agent, or Firm — Banner & Witcoff, Ltd.

(57) ABSTRACT

A staging assembly for a specimen imaging machine includes a manifold assembly with a housing having an inlet opening and an outlet opening. Each of a plurality of chambers has a chamber opening. Conduits put the chambers in fluid communication with the inlet opening and the outlet opening. A bottom plate extends beneath the chambers. The manifold assembly includes an attachment assembly. A staging dock includes a base, a staging dock anesthesia inlet, and a staging dock anesthesia outlet receivable by the inlet opening of the manifold assembly and including a valve. A staging dock exhaust inlet is receivable by the outlet opening of the manifold assembly. The staging dock includes a staging dock exhaust outlet. A staging dock attachment assembly is releasably attachable to the manifold attachment assembly.

25 Claims, 7 Drawing Sheets

STAGING ASSEMBLY FOR SPECIMEN IMAGING SYSTEM

FIELD

Aspects of this disclosure relate generally to a staging assembly for a specimen imaging system, and more particularly, to a staging assembly with a manifold assembly and staging dock for improved delivery and exhaust of anesthesia.

BACKGROUND

Imaging systems are used to examine specimens, e.g., mice and rats, to evaluate the status of medical conditions such as tumors in the specimens. The imaging systems may use X-ray, fluorescence, or bioluminescence, for example, and require that the specimens be immobile during the examination. In order to immobilize the specimens, anesthesia is used.

Prior art imaging systems include an examination chamber in which one or more specimens are individually positioned. Anesthesia, e.g., in the form of a gas, is delivered into a nosecone which is positioned about the snout of the specimen. Waste anesthesia gas is then exhausted from the examination chamber. In some circumstances, the waste anesthesia gas is not fully evacuated from the examination chamber.

Further, when multiple groups of specimens are to be examined, each specimen of each group is individually positioned within the examination chamber, anesthesia is delivered to the specimens, imaging is conducted, and then the group of specimens is removed from the examination chamber. Once the imaging of the first group is completed, the process is repeated for each successive group of specimens.

It would be desirable to provide a staging assembly for a specimen imaging system that reduces or overcomes some or all of the difficulties inherent in prior known devices. Particular objects and advantages will be apparent to those skilled in the art, that is, those who are knowledgeable or experienced in this field of technology, in view of the following disclosure and detailed description of certain embodiments.

SUMMARY

In accordance with a first aspect, a staging assembly for a specimen imaging machine includes a manifold assembly with a housing having an inlet opening and an outlet opening. Each of a plurality of chambers has a chamber opening. Conduits put the chambers in fluid communication with the inlet opening and the outlet opening. A bottom plate extends beneath the chambers. The manifold assembly includes an attachment assembly. A staging dock includes a base, a staging dock anesthesia inlet, and a staging dock anesthesia outlet receivable by the inlet opening of the manifold assembly and including a valve. A staging dock exhaust inlet is receivable by the outlet opening of the manifold assembly. The staging dock includes a staging dock exhaust outlet. A staging dock attachment assembly is releasably attachable to the manifold attachment assembly.

In accordance with another aspect, a staging assembly for an animal imaging machine may include a manifold assembly with a housing having an inlet opening, an inlet conduit in fluid communication with the inlet opening, a plurality of chamber inlet conduits in fluid communication with the inlet conduit, an outlet opening, an outlet conduit in fluid communication with the outlet opening, and a plurality of chamber outlet conduits in fluid communication with the outlet conduit. Each of a plurality of chambers may include a chamber inlet at a top of the chamber and in fluid communication with one of the chamber inlet conduits, a chamber opening, and a pair of chamber outlets, with each chamber outlet positioned on one side and at a bottom of the chamber and extending between the chamber and one of the chamber outlet conduits. A front plate defines the chamber openings, and a bottom plate extends beneath each of the chambers. The manifold assembly includes a manifold attachment assembly. A staging dock includes a base, an anesthesia inlet, a manifold outlet that is receivable by the inlet opening of the manifold assembly and includes a valve. An exhaust inlet is receivable by the outlet opening of the manifold assembly. The staging dock includes an exhaust outlet. A staging dock attachment assembly is releasably attachable to the manifold attachment assembly.

These and additional features and advantages disclosed here will be further understood from the following detailed disclosure of certain embodiments, the drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which.

The figures referred to above are not drawn necessarily to scale, should be understood to provide a representation of particular embodiments, and are merely conceptual in nature and illustrative of the principles involved. Some features of the staging assembly for a specimen imaging system depicted in the drawings have been enlarged or distorted relative to others to facilitate explanation and understanding. The same reference numbers are used in the drawings for similar or identical components and features shown in various alternative embodiments. Staging assemblies for a specimen imaging system as disclosed herein would have configurations and components determined, in part, by the intended application and environment in which they are used.

DETAILED DESCRIPTION OF EMBODIMENTS

In the following description of various example structures in accordance with the disclosure, reference is made to the accompanying drawings, which form a part hereof, and in which are shown by way of illustration of various structures in accordance with the disclosure. Additionally, it is to be understood that other specific arrangements of parts and structures may be utilized, and structural and functional modifications may be made without departing from the scope of the present disclosure. Also, while spatial terms such as "top" and "bottom" and the like may be used in this specification to describe various example features and elements of the disclosure, these terms are used herein as a matter of convenience, e.g., based on the example orientations shown in the figures and/or the orientations in typical use. Nothing in this specification should be construed as requiring a specific three dimensional or spatial orientation of structures in order to fall within the scope of this disclosure.

Figure 1:
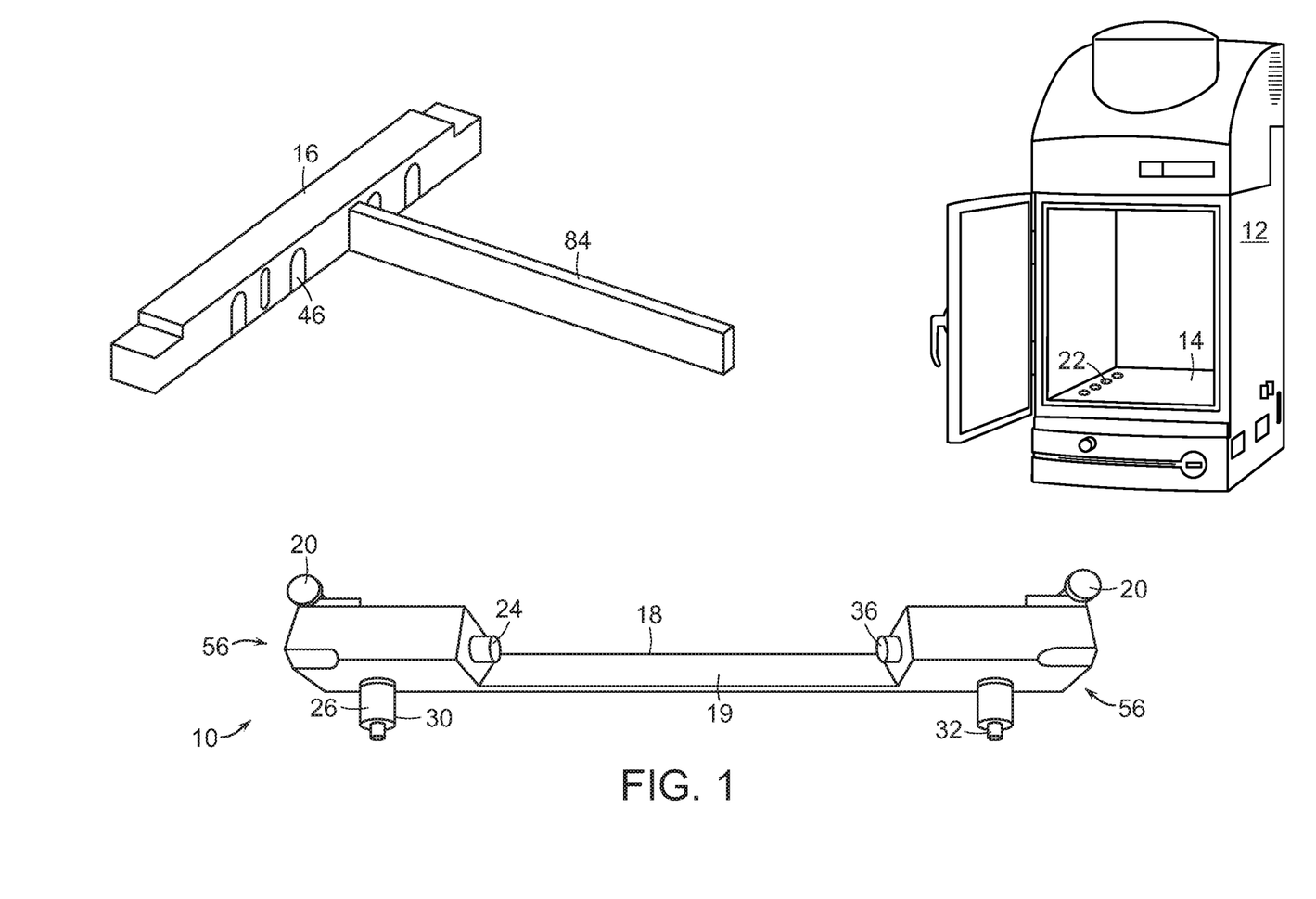
FIG. 1 is a perspective view of a staging assembly including a manifold assembly, a staging dock, and an imaging machine.

Referring to FIG. 1, a staging assembly 10 is shown for using in an imaging machine 12, which includes an imaging chamber 14. Staging assembly 10 includes a manifold assembly 16 that serves to deliver anesthesia to specimens, e.g., mice or rats, and a staging dock 18 to which manifold assembly 16 is attached. As described in greater detail below, anesthesia from an external source is delivered through staging dock 18 and on to manifold assembly 16, which are both positioned in imaging chamber 14. The anesthesia is distributed through manifold assembly 16 to one or more specimens that have been positioned in imaging chamber 14. Imaging of the specimens is performed by imaging machine 12. Waste anesthesia gas is exhausted from manifold assembly 16 and then through staging dock 18 to an exterior of imaging machine 12 by way of an exhaust system either incorporated in imaging machine 12 or external to imaging machine 12. In certain embodiments, imaging machine 12 may include a vacuum system to draw waste anesthesia from manifold assembly 16 and then out of imaging machine 12.

In certain embodiments, staging dock 18 may include a pair of retractable pins 20, shown and described in greater detail below, that are received in apertures 22 formed in a bottom of imaging chamber 14. The engagement of pins 20 within apertures 22 ensures that staging dock 18 is fixed with respect to imaging chamber 14 in a repeatable position, helping improve the accuracy of sequential images being taken of the specimens. In certain embodiments, imaging chamber 14 can include two opposed rows of apertures 22, allowing staging dock 18 to be positioned at different fixed locations within imaging chamber 14.

Staging dock 18 includes a base 19 and a staging dock anesthesia inlet 24 that receives anesthesia from a tube or conduit (not shown) or any other suitable type of connector in imaging chamber 14. The anesthesia travels through base 19 to a staging dock anesthesia outlet 26. Staging dock anesthesia outlet 26 is received by an inlet opening 28 (shown below in FIG. 2) of manifold assembly 16 when manifold assembly 16 is engaged with staging dock 18. Staging dock anesthesia outlet 26 includes a valve 30, shown and described in greater detail below. The anesthesia therefore travels into staging dock 18 through staging dock anesthesia inlet 24, out of staging dock 18 through staging dock anesthesia outlet 26, and then into inlet opening 28 of manifold assembly 16.

Staging dock 18 includes a staging dock exhaust inlet 32 that is received by an outlet opening 34 (shown below in FIG. 2) of manifold assembly 16 when manifold assembly 16 is engaged with staging dock 18. Staging dock 18 also includes a staging dock exhaust outlet 36 that is connected to a tube or conduit (not shown in FIG. 1) or any other suitable type of connector in imaging chamber 14. Waste anesthesia gas is exhausted from manifold assembly 16 through outlet opening 34 of manifold assembly 16 and into staging dock 18 through staging dock exhaust inlet 32. The waste anesthesia gas then exits staging dock 18 through staging dock exhaust outlet 36 and then out through the connector in imaging chamber 14 to an exterior or imaging machine 12.

Figure 2:
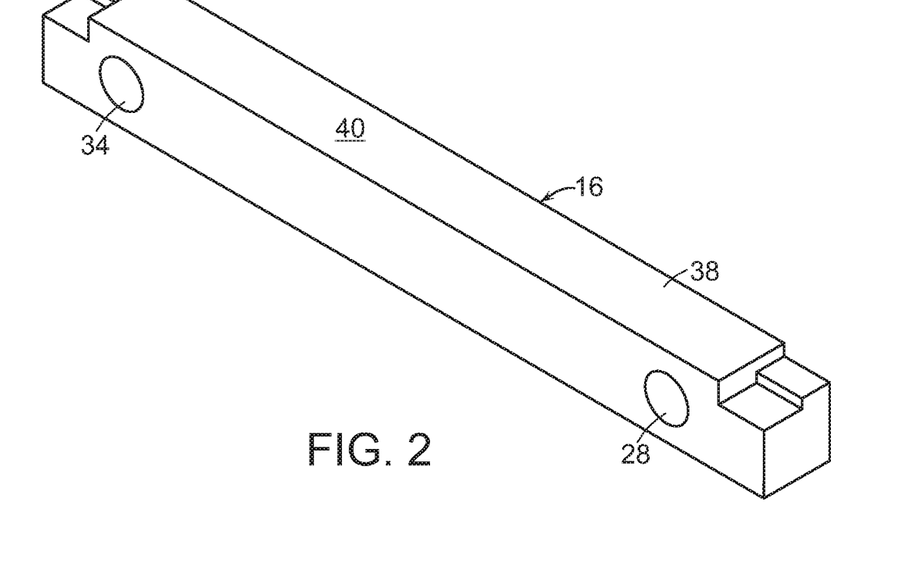
FIG. 2 is a perspective view of a rear of the manifold assembly of FIG. 1.
Figure 3:
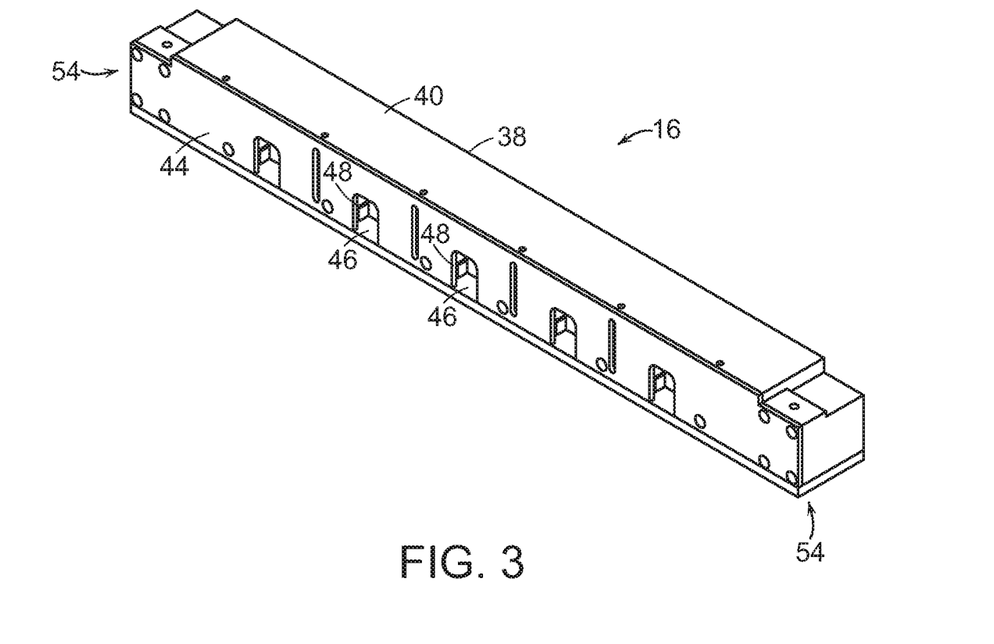
FIG. 3 is a perspective view of a front of the manifold assembly of FIG. 1.
Figure 4:
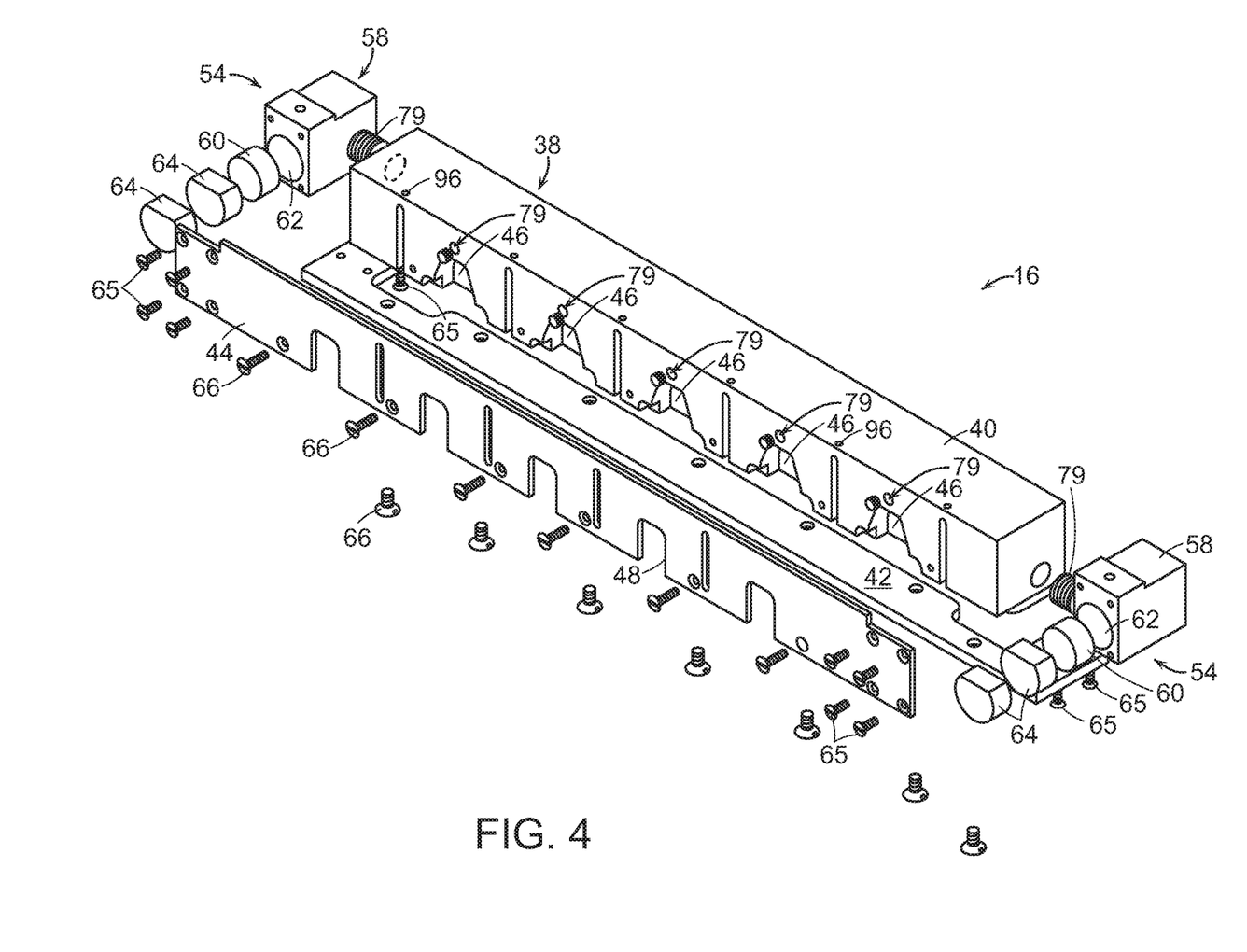
FIG. 4 is an exploded view of the manifold assembly of FIG. 1.

As shown in FIGS. 2-4, manifold assembly 16 includes a housing 38. As noted above, housing 38 includes inlet opening 28 that receives staging dock anesthesia outlet 30 and outlet opening 34 that receives staging dock exhaust inlet 32 when manifold assembly 16 is engaged with staging dock 18.

Housing 38 may include a manifold 40 in which inlet opening 28 and outlet opening 34 are formed, a bottom plate 42, and a front plate 44. It is to be appreciated that all elements of housing 38, as well as other parts of staging assembly 10, may be made of a non-metallic material so as to prevent interference when the imaging system of imaging machine 12 is an X-ray system. Further, all of the elements of housing 38, as well as other parts of staging assembly 10, may be formed of a radiolucent thermoplastic, such as polyoxymethylene, available as Delrin® from E.I. du Pont de Nemours and Company of Wilmington, Del.

Further, it is to be appreciated that all of the elements of staging assembly 10 may be black, non-reflective, and/or non-fluorescent in order to reduce reflectivity and help produce better images in imaging chamber 12.

A plurality of chambers 46 are formed in manifold 40, with each chamber having an opening 48 formed in front plate 44. Chambers 46 are in fluid communication with inlet opening 28 and outlet opening 34 thereby allowing anesthesia to flow into chambers 46 and waste anesthesia to flow out of chambers 46. Openings 48 are configured and sized to receive at least a portion of a snout of a specimen such as a mouse or a rat.

In certain embodiments, manifold assembly 16 may include a manifold attachment assembly 54, shown more clearly in FIG. 4 where manifold assembly 16 is shown in exploded form. Manifold attachment assembly 54 works in conjunction with a staging dock attachment assembly 56, shown in FIG. 1, to releasably secure manifold assembly 16 to staging dock 18. In certain embodiments, manifold attachment assembly 54 and staging dock attachment assembly 56 may use magnets to secure manifold assembly 16 to staging dock 18.

In the illustrated embodiment, magnet blocks 58 are secured to front plate 44 and bottom plate 42 at ends of manifold 40. Magnets 60 are seated in apertures 62 formed in magnet blocks 58. Foam plugs 64 may be inserted into apertures 62 outward of magnets 60. Magnet blocks 58 may be secured to front plate 44 and bottom plate 42 with screws 65

In certain embodiments, magnet blocks 58 are formed of a metal, such as aluminum, for example. Magnets 60 may be formed of neodymium, for example. Other suitable materials for magnet blocks 58 and magnets 60 will become readily apparent to those skilled in the art, given the benefit of this disclosure.

In certain embodiments, staging dock attachment assembly 56 may also include magnets oriented with a pole opposite of that of magnets 60. In other embodiments, staging dock attachment assembly 56 may simply include a piece of magnetic or ferrous material to which magnets 60 can be releasably secured. In certain embodiments, staging dock attachment assembly 56 could include magnets 60 while manifold attachment assembly 54 could simply include a magnetic or ferrous piece of material. Thus, at least one of manifold attachment assembly 54 and staging dock attachment assembly 56 includes magnets.

Bottom plate 42 and front plate 44 may be secured to manifold 40 with bolts or screws 66 or other suitable fasteners. Screws 66 may be formed of a radiolucent material, such as nylon, for example.

Figure 5:
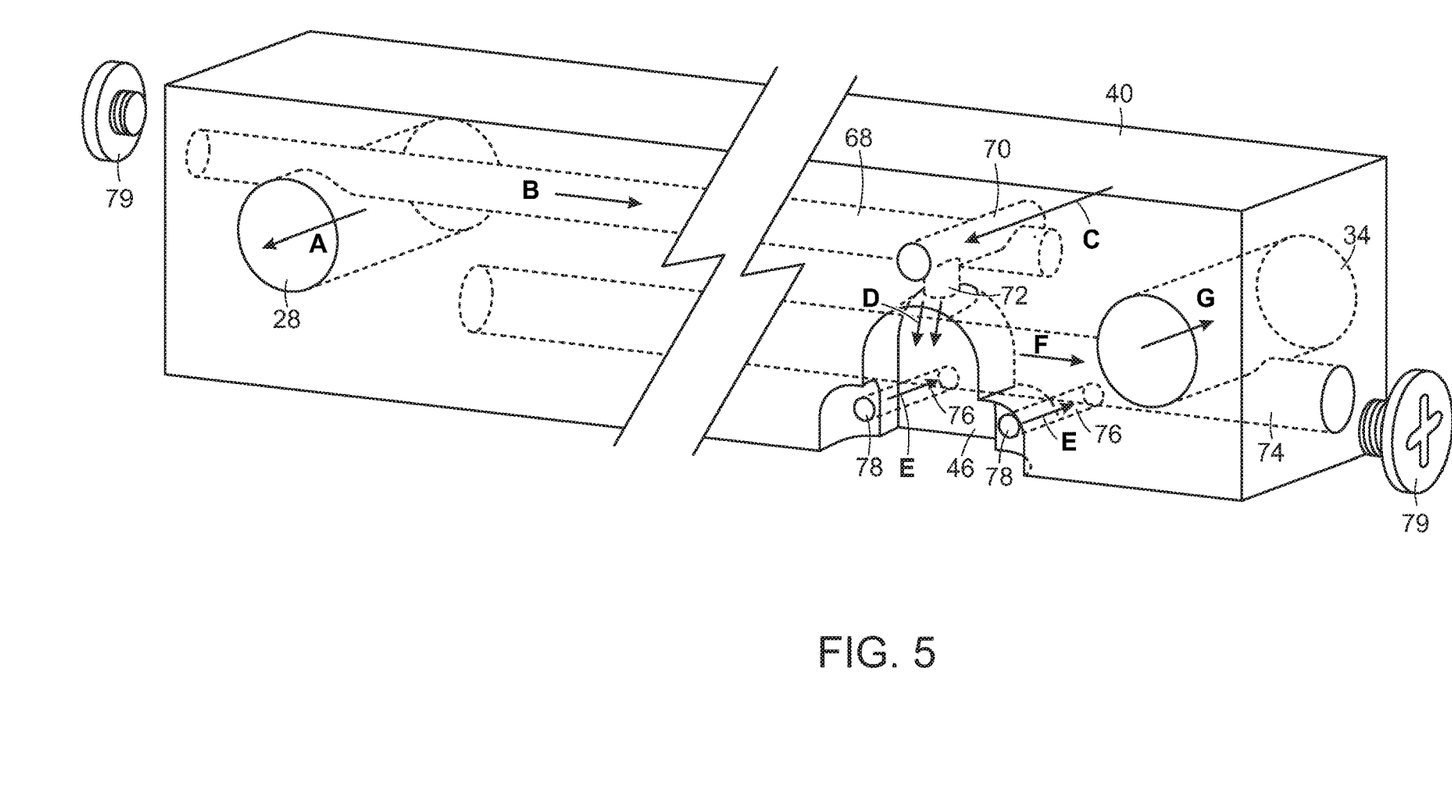
FIG. 5 is a schematic view of a manifold of the manifold assembly of FIG. 1.

As seen in greater detail in FIG. 5, manifold 40 includes an inlet conduit 68 that is in fluid communication with inlet opening 28. A plurality of chamber inlet conduits 70 are in fluid communication with inlet conduit 68. Each chamber 46 has a chamber inlet 72 at a top thereof that is in fluid communication with one of the chamber inlet conduits 70.

Thus, anesthesia can flow into inlet opening 28 of manifold 40 in the direction of arrow A, through inlet conduit 68 in the direction of arrow B, through chamber inlet conduits 70 in the direction of arrow C, and then downwardly into chambers 46 through chamber inlets 72 in the direction of arrows D.

Manifold 40 also includes an outlet conduit 74 in fluid communication with outlet opening 34. A plurality of chamber outlet conduits 76 are in fluid communication with outlet conduit 74. Each chamber 46 has a pair of chamber outlets 78, with each chamber outlet 78 in fluid communication with one of the chamber outlet conduits 76. In the illustrated embodiment, each chamber outlet 78 is positioned at a bottom of chamber 46 and at one side thereof.

Thus, waste anesthesia can flow out of chamber outlets 78 in chamber 46 into chamber outlet conduits 76 in the direction of arrows E, through outlet conduit 74 in the direction of arrow F, and then out of manifold 40 through outlet opening 34 in the direction of arrow G. In certain embodiments, a constant vacuum is maintained in manifold 40 in order to ensure that waste anesthesia is continuously evacuated from chambers 46.

This configuration provides an efficient delivery of anesthesia to the specimens, whose snouts are positioned through openings 48 into chambers 46, as well as an efficient exhaust of waste anesthesia from chambers 46, thereby reducing the chance of exposure of users to the anesthesia.

In certain embodiments, manifold 40 is a solid block of material and inlet conduit 68, chamber inlet conduits 70, chamber inlets 72, chamber outlet conduits 76, outlet conduit 74, and outlet opening 34 are bores that are drilled into manifold 40. It is to be appreciated that manifold 40 need not necessarily be formed as a solid block, and that the various conduits and inlets can be separate members, such as pipes or tubes, that are connected to one another.

In such embodiments where the conduits are bores in manifold 40, plugs 79 may be inserted into ends of inlet conduit 68, outlet conduit 74 and chamber inlet conduits 70, as illustrated in FIGS. 4 and 5. In certain embodiments, plugs 79 may be set screws. Plugs 79 may be formed of a radiolucent material, such as nylon, or of stainless steel, for example.

Figure 6:
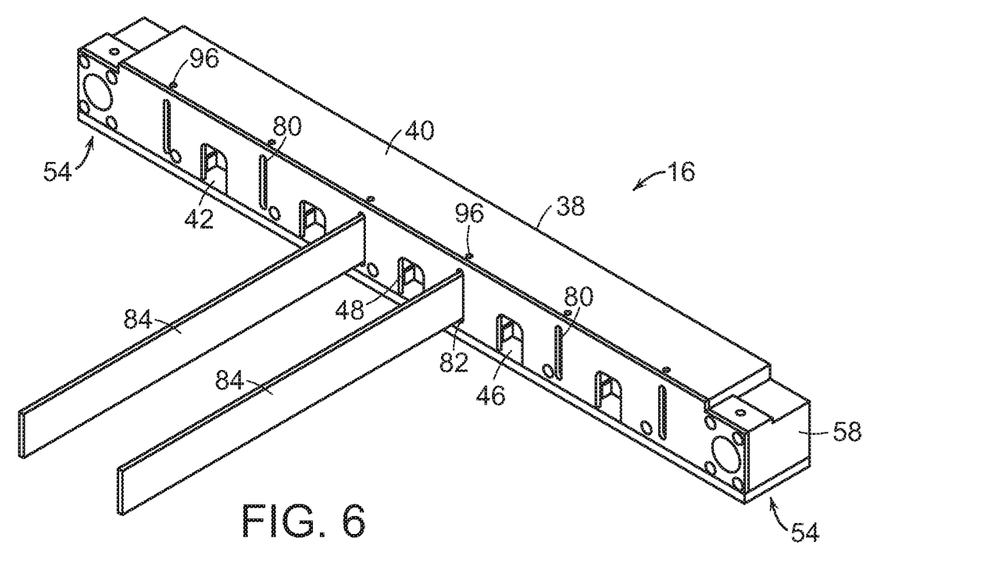
FIG. 6 is a perspective view of a front of the manifold assembly of FIG. 1, shown with a plurality of baffles.

As shown in FIG. 6 a plurality of apertures or slots 80 are formed in front plate 44. A first end 82 of each of one or more baffles 84 may be received in one of the slots 80. Baffles 84 serve to separate the specimens from one another when they are positioned in imaging chamber 14, with each of their respective snouts being received in one of the chamber openings 48 formed in front plate 44.

Figure 7:
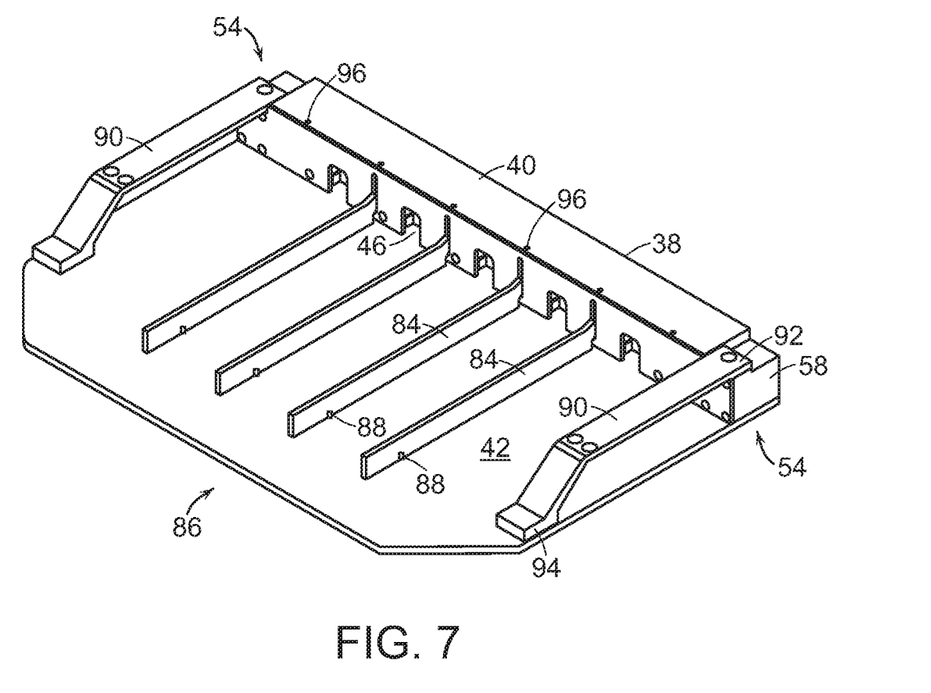
FIG. 7 is a perspective view of staging tray to be used with the staging assembly of FIG. 1.
Figure 8:
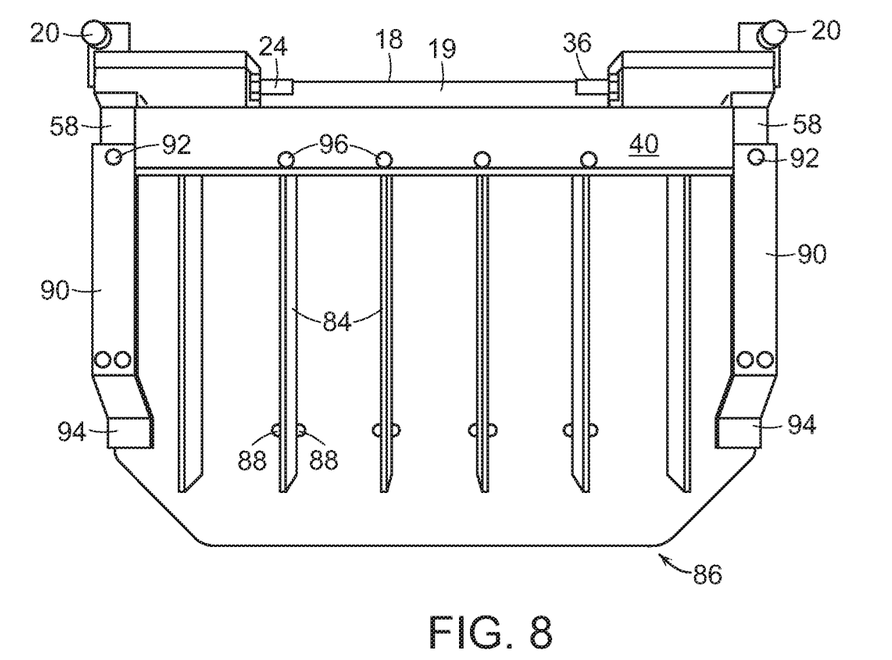
FIG. 8 is a plan view of the staging tray of FIG. 7.

In certain embodiments, as illustrated in FIGS. 7 and 8, bottom plate 42 may extend outwardly from manifold 40 so as to form a staging tray 86, and baffles 84 may extend along and be seated on bottom plate 42. FIG. 8 illustrates staging tray in its engaged position with staging dock 18.

Staging tray 86 allows a user to prepare specimens for imaging before they need to be positioned in imaging chamber 14. Thus, while a first set of specimens is positioned within imaging chamber 14, a second set of specimens can be properly posed on staging tray 86. After imaging of the first set of specimens is complete and that set of specimens is removed from imaging chamber 14, staging tray 86 with the second set of specimens can be secured to staging dock 18 in imaging chamber 14 as described above.

A plurality of pairs of dowels or pins 88 may extend upwardly from bottom plate 42, with each baffle being positioned between and abutting each pin 88 of one of the pairs of pins 88. Pins 88 serve to keep baffles 84 aligned and in proper position on staging tray 86. In certain embodiments, pins 88 are formed of metal, such as stainless steel, for example. Pins 88 may be black passivated stainless steel to reduce reflectivity and help produce better images.

In the illustrated embodiment, four baffles 84 are positioned along staging tray 86, allowing for 5 specimens to be posed on staging tray 86. It is to be appreciated that more or fewer than four baffles 84 can be positioned along staging tray 86.

In certain embodiments, staging tray 86 may include a pair of handles 90 that are screwed, welded, glued, bolted, or otherwise secured to staging tray 86. A first end 92 of each handle 90 may be secured to magnet block 58 while a second end 94 of each handle 90 may be secured to bottom plate 42. In certain embodiments, handles 90 are formed of a metal, such as aluminum, and may be black anodized. In certain embodiments, second end 94 may be a separate piece of material secured to first end 92, and may be formed of a black thermoplastic, such as polyoxymethylene, available as Delrin® from E.I. du Pont de Nemours and Company of Wilmington, Del.

In certain embodiments, a plurality of fiducial elements 96 are positioned along a top surface of manifold 40. Fiducial elements 96 serve as reference points for positioning of staging tray 86 and the specimens in imaging machine 12.

Figure 9:
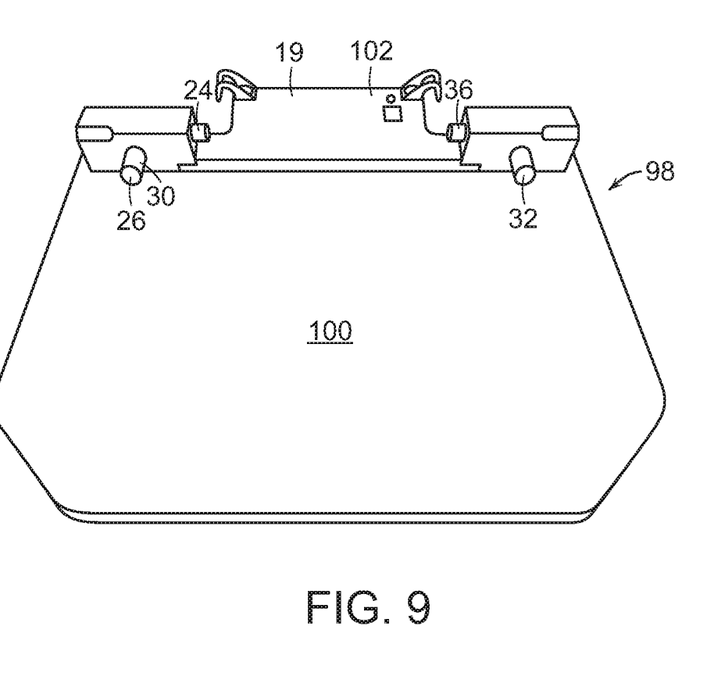
FIG. 9 is a perspective view of a posing station to be used with the staging tray of FIG. 7.

As illustrated in FIG. 9, staging assembly 10 may also include a posing station 98. Posing station 98 may include a tray 100 and a posing station staging dock 102. Posing station staging dock 102 has the same components as that of staging dock 18 since it operates in the same fashion. However, posing station staging dock 102 is not connected to the anesthesia source and vacuum source in imaging machine 12, but rather to an external anesthesia source and an external vacuum. Further, since posing station staging dock 102 is not positioned in imaging machine 12, it does not necessarily include retractable pins 20, as seen in the embodiment illustrated in FIG. 9.

In some embodiments, tray 100 may be heated to maintain a suitable body temperature for the specimens while they are under anesthesia. In certain embodiments, tray 100 may be heated so that the specimens' body temperature is maintained at approximately 37° C.+/−2° C.

A staging tray 86 can be connected to posing station staging dock 102 in order to properly pose or position specimens prior to placement of the specimens in imaging machine 12. This can increase throughput since a user can properly pose or position specimens on a staging tray 86 and keep the specimens anesthetized while another set of specimens is undergoing imaging in imaging machine 12. Once the imaging of the specimens in imaging machine 12 has been completed, the staging tray 86 can be disconnected from posting station 98 and connected to the staging dock 18 in imaging machine 12 in order to produce images of the specimens on staging tray 86.

It is to be appreciated that staging assembly 10 could include a plurality of staging trays 86 in order to properly position and prepare specimens. This will increase throughput as it will reduce or eliminate waiting times.

Figure 10:
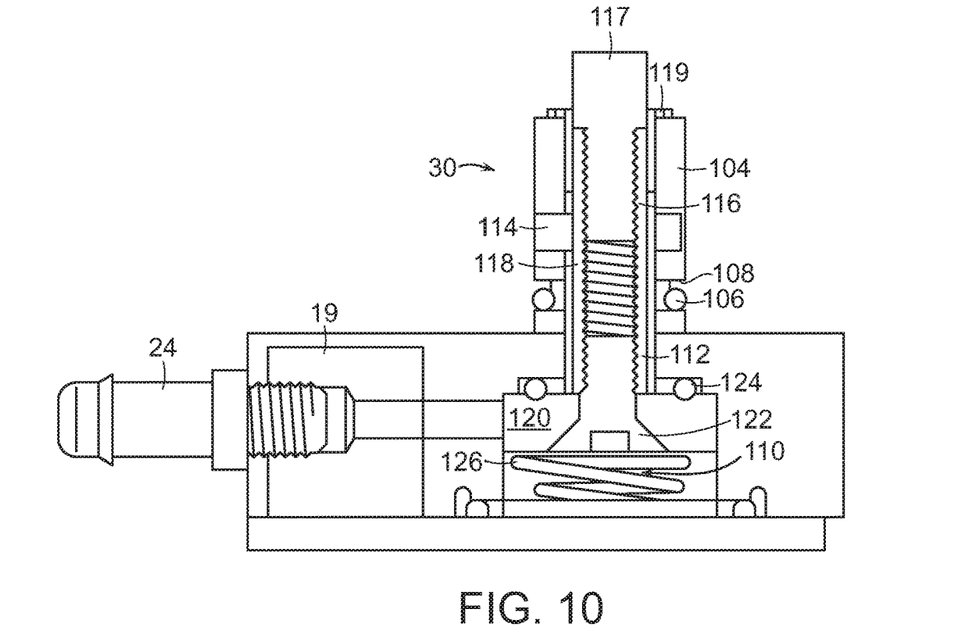
FIG. 10 is a section view of a valve of the staging dock of FIG. 1, shown in a closed condition.
Figure 11:
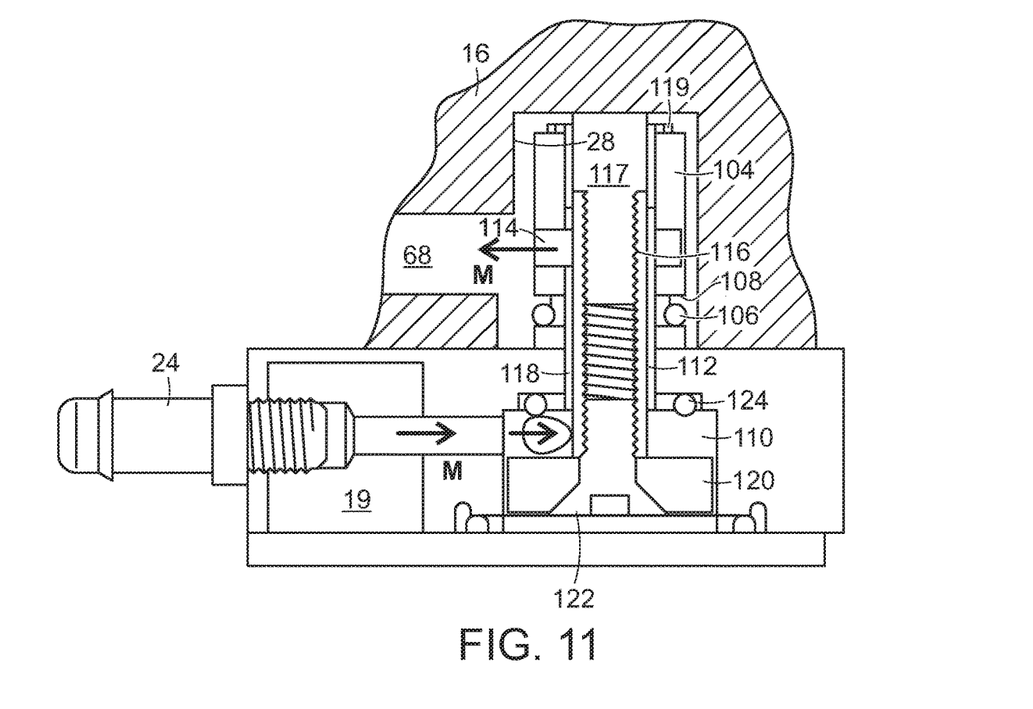
FIG. 11 is a section view of a valve of the staging dock of FIG. 1, shown in a open condition.

An embodiment of staging dock anesthesia outlet 26 with valve 30 is illustrated in FIGS. 10-11. As described in greater detail below, valve 30 is shown in its closed position in FIG. 10, and in its open position in FIG. 11, where it is seen in engagement with staging dock 18.

Valve 30 may include a valve body 104, which is received in inlet opening 28 of manifold assembly 16, as seen in FIG. 11. An O-ring 106 may be provided in a groove 108 formed in an exterior surface of valve body 104 to provide a sealing engagement between valve body 104 and inlet opening 28. In certain embodiments, and O-ring may also be provided on the exterior of staging dock exhaust inlet 32.

A cavity 110 formed in staging dock 18 is in fluid communication with anesthesia inlet 24 of staging dock 18. Valve body 104 includes a cylindrical opening 112 that is in fluid communication with cavity 110. An aperture 114 formed in valve body 104 is in fluid communication with cylindrical opening 112 and an exterior of valve body 104. Thus, a fluid path is formed from anesthesia inlet 24 through cavity 110, cylindrical opening 112, aperture 114 and inlet opening 28, allowing anesthesia to flow from the anesthesia source, through valve 30, and into staging dock 18.

Valve 30 includes a shaft 116 having a first end and a second end that is movably received in cylindrical opening 112, and defines a gap 118 between shaft 116 and cylindrical opening 112. A cap 117 is secured to the second end of shaft 116 such as by a threaded engagement between cap 117 and shaft 116, for example. A bearing 119 may seated in gap 118 between the second end of shaft 116 and the outer end of valve body 104, thereby helping to center shaft 116 and cap 117. Bearing 119 may be formed of a low friction material, such as nylon, for example.

A plug 120 is seated in cavity 110 and is secured to the first end of shaft 116 by way of a screw or sealing screw 122. Sealing screw 122 may include an O-ring (not shown) in order to reduce leakage. A sealing member such as a gasket 124 is seated in cavity 110 between plug 120 and gap 118. A spring 126 is seated in cavity 110, and biases plug 120 into sealing engagement with gasket 124 with when valve 30 is in the closed condition, as seen in FIG. 10. In certain embodiments, spring 126 may be a conical spring.

As illustrated in FIG. 11, when manifold assembly 16 is engaged with staging dock 18, cap 117 engages an interior surface of inlet opening 28, thereby depressing cap 117, shaft 116, plug 120, and sealing screw 122 against the biasing pressure of spring 126, and moving plug 120 out of sealing engagement with gasket 124. There is now a clear path for the anesthesia to flow from inlet opening 28 into cavity 110, upwardly through gap 118 and out of aperture 114 into inlet opening 28 and onward to inlet conduit 68, as illustrated by the arrows M.

Those having skill in the art, with the knowledge gained from the present disclosure, will recognize that various changes can be made to the disclosed apparatuses and methods in attaining these and other advantages, without departing from the scope of the present disclosure. As such, it should be understood that the features described herein are susceptible to modification, alteration, changes, or substitution. For example, it is expressly intended that all combinations of those elements and/or steps which perform substantially the same function, in substantially the same way, to achieve the same results are within the scope of the embodiments described herein. Substitutions of elements from one described embodiment to another are also fully intended and contemplated. The specific embodiments illustrated and described herein are for illustrative purposes only, and not limiting of that which is set forth in the appended claims. Other embodiments will be evident to those of skill in the art. It should be understood that the foregoing description is provided for clarity only and is merely exemplary. The spirit and scope of the present disclosure is not limited to the above examples, but is encompassed by the following claims. All publications and patent applications cited above are incorporated by reference in their entirety for all purposes to the same extent as if each individual publication or patent application were specifically and individually indicated to be so incorporated by reference.

What is claimed is:

1. A staging assembly for a specimen imaging machine comprising:
   a manifold assembly comprising:
     a housing having an inlet opening and an outlet opening;
     a plurality of chambers, each chamber having a chamber opening positioned at a front of the housing;
     a plurality of conduits putting the chambers in fluid communication with the inlet opening and the outlet opening;
     a bottom plate extending beneath each of the chambers; and
     a manifold attachment assembly; and
   a staging dock comprising:
     a base;
     a staging dock anesthesia inlet;
     a staging dock anesthesia outlet receivable by the inlet opening of the manifold assembly and including a valve;
     a staging dock exhaust inlet receivable by the outlet opening of the manifold assembly;
     a staging dock exhaust outlet; and
     a staging dock attachment assembly releasably attachable to the manifold attachment assembly to releasably attach a front of the staging dock to a rear of the housing.

2. The staging assembly of claim 1, further comprising a plurality of baffles releasably secured to the manifold assembly housing, each baffle positioned between adjacent chamber openings.

3. The staging assembly of claim 2, wherein the bottom plate extends outwardly from the manifold assembly to form a staging tray.

4. The staging assembly of claim 3, further comprising a plurality of pairs of pins, each pin extending upwardly from the bottom plate of the staging tray, each baffle being positioned between and abutting each pin of one of the pairs of pins.

5. The staging assembly of claim 3, further comprising a pair of handles secured to a top surface of the bottom plate.

6. The staging assembly of claim 3, further comprising a plurality of slots formed in a front surface of the manifold assembly housing, each slot configured to receive one of the baffles.

7. The staging assembly of claim 3, wherein the manifold assembly includes four baffles.

8. The staging assembly of claim 1, wherein the staging dock includes a pair of retractable pins extendable downwardly from the base.

9. The staging assembly of claim 1, wherein at least one of the manifold attachment assembly and the staging dock attachment assembly comprises a pair of magnets.

10. The staging assembly of claim 1, further comprising a plurality of fiducial elements positioned along the manifold assembly above the chambers.

11. The staging assembly of claim 10, wherein the fiducial elements are formed of a non-fluorescent radiolucent material.

12. The staging assembly of claim 1, further comprising a posing station comprising:
a posing tray;
a posing station anesthesia inlet;
a posing station anesthesia outlet receivable by the inlet opening of the manifold assembly and including a valve;
a posing station exhaust inlet receivable by the outlet opening of the manifold assembly;
a posing station exhaust outlet; and
a posing station attachment assembly releasably attachable to the manifold attachment assembly.

13. The staging assembly of claim 12, wherein at least one of the manifold attachment assembly and the posing station attachment assembly comprises a pair of magnets.

14. The staging assembly of claim 12, wherein the posing tray is heated.

15. The staging assembly of claim 1, wherein the valve comprises:
a valve body including a cylindrical opening in fluid communication with a cavity formed in the base of the staging dock, the cavity being in fluid communication with the anesthesia inlet, and an aperture in fluid communication with the cylindrical opening and an exterior of the valve body;
a shaft movably received in the cylindrical opening to define a gap between the shaft and the cylindrical opening, and a plug at a first end of the shaft and movably received within the cavity;
a spring seated in the cavity and biasing the plug toward the gap; and
a sealing member positioned between the plug and the gap.

16. The staging assembly of claim 15, wherein the spring is a conical spring.

17. The staging assembly of claim 15, further comprising an O-Ring seated in a groove formed in an exterior surface of the housing.

18. The staging assembly of claim 15, wherein the sealing member is a gasket.

19. The staging assembly of claim 15, further comprising a cap at a second end of the shaft.

20. The staging assembly of claim 19, further comprising a bearing positioned in an end of the gap between the cap and the valve body.

21. A staging assembly for an animal imaging machine comprising:
a manifold assembly comprising:
a housing having an inlet opening, an inlet conduit in fluid communication with the inlet opening, a plurality of chamber inlet conduits in fluid communication with the inlet conduit, an outlet opening, an outlet conduit in fluid communication with the outlet opening, and a plurality of chamber outlet conduits in fluid communication with the outlet conduit;
a plurality of chambers, each chamber including a chamber inlet at a top of the chamber and in fluid communication with one of the chamber inlet conduits, a chamber opening positioned at a front of the housing, and a pair of chamber outlets, each chamber outlet positioned on one side and at a bottom of the chamber and extending between the chamber and one of the chamber outlet conduits;
a front plate defining the chamber openings;
a bottom plate extending beneath each of the chambers;
a manifold attachment assembly; and
a plurality of baffles releasably secured to the housing, each baffle positioned between adjacent chamber openings; and
a staging dock comprising:
a base;
an anesthesia inlet;
a manifold outlet receivable by the inlet opening of the manifold assembly and including a valve;
an exhaust inlet receivable by the outlet opening of the manifold assembly;
an exhaust outlet; and
a staging dock attachment assembly releasably attachable to the manifold attachment assembly to releasably attach a front of the staging dock to a rear of the housing.

22. The staging assembly of claim 21, further comprising a manifold block received in the housing, wherein the inlet opening, the inlet conduit, the outlet opening, the outlet conduit, the chamber inlet conduits, and the chamber outlet conduits comprise bores extending through at least a portion of the manifold block.

23. The staging assembly of claim 22, further comprising a plurality of plugs, one of the plugs being inserted into an end of each of the inlet conduit, the outlet conduit, and the chamber inlet conduits.

24. The staging assembly of claim 23, wherein the plugs comprise screws.

25. The staging assembly of claim 24, wherein at least some of the screws are formed of a radiolucent material.

* * * * *